United States Patent [19]

Ogawa et al.

[11] Patent Number: 5,759,161
[45] Date of Patent: Jun. 2, 1998

[54] MEDICAL WIRE AND METHOD FOR LEAVING IMPLANTED DEVICES

[75] Inventors: Atsushi Ogawa, Odawara; Waro Taki, Osaka; Akiyo Sadato, Kyoto, all of Japan

[73] Assignee: Kaneka Medix Corporation, Osaka, Japan

[21] Appl. No.: 638,486

[22] Filed: Apr. 26, 1996

[51] Int. Cl.$^6$ ........................... A61B 5/00
[52] U.S. Cl. ........................... 600/585
[58] Field of Search ........... 128/772; 606/32, 606/41

[56] References Cited

U.S. PATENT DOCUMENTS

| | | | |
|---|---|---|---|
| 4,346,712 | 8/1982 | Handa et al. | 128/325 |
| 4,402,319 | 9/1983 | Handa et al. | 128/305 |
| 5,122,136 | 6/1992 | Guglielmi et al. | 606/32 |
| 5,498,227 | 3/1996 | Mawad | 600/3 |

FOREIGN PATENT DOCUMENTS

| | | |
|---|---|---|
| 60-30225 | 7/1985 | Japan. |
| 2-31993 | 7/1990 | Japan. |
| 5-500322 | 1/1993 | Japan. |

*Primary Examiner*—Max Hindenburg
*Attorney, Agent, or Firm*—Frishauf, Holtz, Goodman, Langer & Chick

[57] ABSTRACT

A medical wire includes a conductive wire body and an implanted device connected to the distal end of the wire body through a joint member. The medical wire is inserted through a patient's tubular organ, thereby guiding the implanted device to the intended site in the patient's body. In this state, a monopolar high-frequency current is applied to the joint member through the wire body, thereby heating the joint member to cause it melt and sever, whereby the implanted device is detached from the wire body. There are thus provided a medical wire having an implanted device, which permits depositing the implanted device at the intended site in the patient's body by a simple operation within a short period of time, a mechanism which is simple in structure and highly reliable, and a method for depositing the implanted device of the medical wire is also provided.

18 Claims, 3 Drawing Sheets

F I G. 5
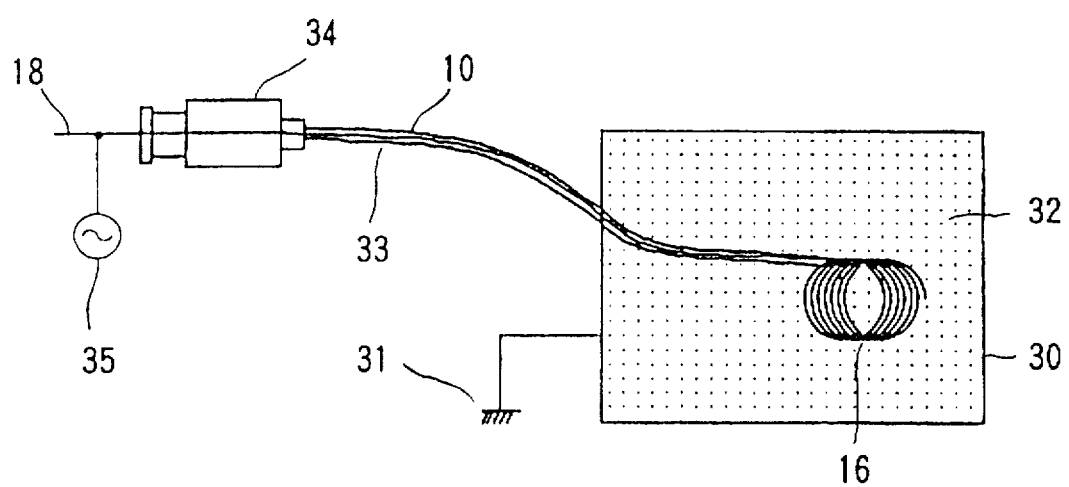

MEDICAL WIRE AND METHOD FOR LEAVING IMPLANTED DEVICES

BACKGROUND OF THE INVENTION

1) Field of the Invention

The present invention relates to a medical wire used to deposit an implanted device at an intended site in a patient's body through a tubular organ thereof, and a method for depositing the implanted devices.

2) Description of the Background Art

Various problems are generally presented in treatment involving surgery to a patient's body. For example, the patient undergoing an operation must withstand the long hours of stress of the procedure. The surgeon, as well, is forced to endure intense concentration for the long period of operation. The danger of infection is always a possibility.

In order to lighten such stress and to perform a necessary operation safely and easily, various medical instruments such as catheters, guide wires and embolizing materials for occluding tubular organs such as vessels have recently been developed and been put to practical use.

With recent advancement in medical instruments such as catheters and guide wires, an endovascular operation in which the intended diseased part is approached through a vessel is currently often performed in the treatment of diseases such as arteriovenous malformation, cerebral aneurysm and carotid-cavernous fistula.

At the present time, releasable balloons, coils, liquid embolizing substances, particulate embolizing substances and the like are used as tubular organ embolizing materials. Once such an embolizing material is left or released at an erroneous or undesirable site in a tubular organ, however, it is generally next to impossible to recover or to change the site.

Under such circumstances, proposals have heretofore been made for releasable embolizing materials, by which an embolizing material can be pulled back and reinserted even when one fails to deposit it at the intended site, and can be released and left after confirmation of the disposed site.

For example, Japanese Patent Application Laid-Open No. 500322/1993 (though PCT route) proposed a method for leaving a thrombus-forming member in an aneurysm, wherein the thrombus-forming member is provided at the distal end of the guide wire with a joint member made of stainless steel, the thrombus-forming member is deposited at the intended site, and the joint member is then severed, thereby detaching the thrombus-forming member from the guide wire.

In this method, a positive current is applied to the guide wire, thereby forming a thrombus around the thrombus-forming member, and at the same time, electrolyzing the joint member made of stainless steel situated at the distal end of the guide wire causing the thrombus-forming member to detach from the guide wire.

However, this method presents the problem of iron ions, nickel ions and fragments of the stainless steel member formed by the electrolysis thereof and released in the patient's body.

Furthermore, from a practical viewpoint, the method is problematic because it takes several minutes to electrolyze one joint member of stainless steel to make it sever. Moreover, when several thrombus-forming members are inserted in the same aneurysm, the time required for detaching the thrombus-forming members is further lengthened because the surface area of conductive parts increases. In some cases, it may take 15 to 30 minutes to electrolyze them.

If it takes a long time to detach the implanted devices as described above, the operation is lengthened, which imposes a great burden on the patient and doctor.

Japanese Patent Application Laid-Open No. 43962/1981 proposed constructing a medical guide by bonding an implanted balloon to the distal end of a catheter through a joint member composed of, for example, polyvinyl alcohol, placing heating electrodes at the joint member and arranging lead wires extending to these heating electrodes in a catheter. According to such construction, the joint member is melted and severed by applying a current to the heating electrodes, thereby detaching the balloon from the catheter. However, this technique requires suitable electrodes at the joint member, complicating the structure of such a part. In addition, two lead wires extending to the heating electrodes must be inserted into the catheter, and the lead wires may possibly be broken because fine wires are used.

As described above, all the conventional implanted devices involve problems in term of the time it takes to leave the implanted device, the complex structure and the intricacy of the operation required to be performed.

SUMMARY OF THE INVENTION

It is therefore the aim of the present invention to provide a medical wire having an implanted device, which permits leaving the implanted device at the intended site in a patient's body by means of a simple operation within a short period of time, and which uses a simple structure which is highly reliabile.

Another aim of the present invention is to provide a method for leaving the implanted devices at the intended site in a patient's body by using the above medical wire having an implanted device.

The above objects can be achieved by the present invention described below.

According to the present invention, there is thus provided a medical wire having an implanted device, comprising:
 a conductive wire body; and an implanted device connected to the distal end of the wire body through a joint member, wherein the joint member is heated by applying a monopolar high-frequency current through the wire body, whereby the implanted device becomes detached from the wire body.

In the above medical wire, the material of the joint member should preferably be poly(vinyl alcohol) or a vinyl alcohol copolymer.

The wire body should preferably be made by closely winding wire on the peripheral surface of a core wire to form a coil.

The surface of the wire body should preferably be covered with an electrically insulating coating.

A coil piece formed of an elastic material that is pliable should preferably be used as the implanted device. The present invention also provides a method for depositing the implanted device in a patient's body, comprising the following steps:
 inserting a medical wire, which is comprised of a conductive wire body to a distal end of which the implanted device is connected with a joint member, through a vital tubular organ, thereby guiding the implanted device to the intended site in the patient's body; and
 applying a monopolar high-frequency current to the joint member through the wire body, thereby heating the joint member causing it to melt and sever, whereby the implanted device is detached from the wire body.

The medical wire, according to the present invention, is inserted into the patient's body through a tubular organ thereof with or without using a catheter, whereby the implanted devices provided at the distal end of the wire body is disposed at the intended site. In this state, a monopolar or unipolar high-frequency current is applied to the joint member through the wire body utilizing the conductivity of the wire body, thereby heating the joint member. As a result, the implanted device is detached from the wire body to be left in the patient's body.

As described above, the implanted device is detached by heating the joint member. According to the present invention, therefore, the time required to leave the implanted device in a patient's body is extremely short.

When the joint member comprises polyvinyl alcohol or a vinyl alcohol copolymer, the joint member can be severed by heating, whereby the implanted device is detached from the wire body. Therefore, the depositing procedure becomes easy and reliable.

BRIEF DESCRIPTION OF THE DRAWINGS

The above and other objectives, features and advantages of the present invention will become apparent from the following description and the appended claims, taken in conjunction with the accompanying drawings, in which:

FIG. 5 schematically illustrates an experiment in leaving the implanted device using the medical wire of FIG. 1.

DETAILED DESCRIPTION OF THE PREFERRED EMBODIMENTS

The present invention will hereinafter be described in detail according to the embodiments of the present invention.

Figure 1:
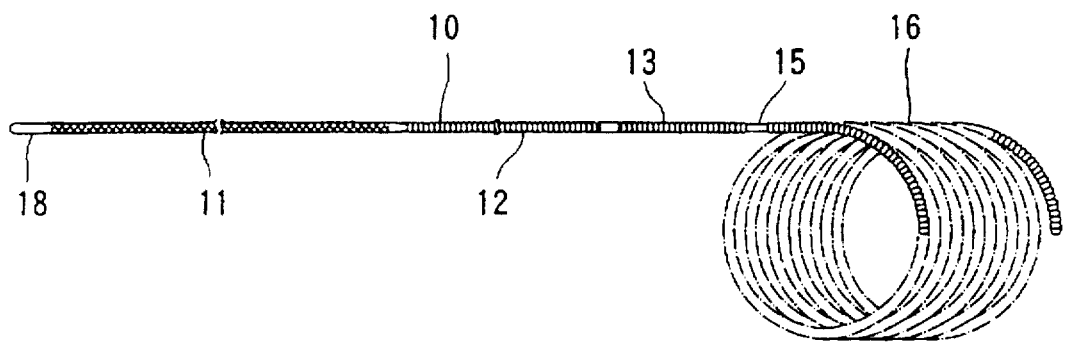
FIG. 1 illustrates a construction of a medical wire having an implanted device which is an embodiment of the present invention.

FIG. 1 illustrates a construction of a medical wire which is an embodiment of the present invention. The medical wire in this embodiment basically comprises a wire body 10 made of metal, a joint member 15 in the form of a short rod, which is connected at its proximal end to the distal end of the wire body 10 and can be severed by heating, and an implanted device 16 connected to the distal end of the joint member 15.

The illustrated wire body 10 comprises a proximal part 11 with an insulating coating, a flexible part 12 connected thereto, and a distal X-ray impervious part 13 connected to the flexible part 12. The joint member 15 is connected to the tip of the X-ray impervious part 13.

The flexible part 12 and distal X-ray impervious part 13 of the wire body 10 are constructed by, for example, closely winding a winding wire on the peripheral surface of a core wire to form a coil.

The wire body 10 preferably has an outer diameter of 0.1 to 2.0 mm, while the core wire preferably has an outer diameter of 0.03 to 2.0 mm. In addition, a wire having an outer diameter of 0.01 to 0.2 mm is preferably used as the winding wire. The winding wire is preferably wound at a pitch equal to its diameter, for example, in one to three layers. The length of the wire body 10 may be varied according to the intended application and could be 0.1 to 1.8 mm by way of example.

The wire body 10 constructed by closely winding a wire on the peripheral surface of the core wire in the form of a coil as described above is preferred since it combines sufficient flexibility with the strength and stiffness required for its insertion though it has a adequately thin outer diameter.

A conductive metallic material such as stainless steel, titanium-nickel alloy, platinum or copper may be used as a wire for the wire body 10, with stainless steel particularly preferred. A wire composed of a metal such as platinum, copper or tungsten may be used in the distal X-ray impervious part.

The surface insulating coating in the proximal part 11 of the wire body 10 may be formed of any suitable material. However, it may be generally formed of one of various resins, for example, a fluorocarbon resin or hydrophilic resin. The surface insulated coating composed of a fluorocarbon resin or hydrophilic resin is preferred becouse the coefficient of friction with the surface can be low.

The proximal part 11 is constructed such that at the most proximal end thereof, the wire is exposed to form a terminal part 18 through which electric current can be applied via suitable conductive members such as an electrical connector, plug and/or clip.

For example, about 1 to 3 cm will suffice for the length of this terminal part 18.

No limitation is imposed on the material for the joint member 15 as long as it does not adversely affect the patient's body and can be severed by heating to detach the implanted device 16 from the wire body 10. Specifically, polyvinyl alcohol or a vinyl alcohol copolymer, which melts and severs by itself with heat, is preferred.

However, the material for the joint member 15 is not limited to this polymer. For example, a material such as a shape-memory alloy or resin, which is deformed by heating, may be used.

When the joint member 15 is in the form of a rod composed of the poly(vinyl alcohol) or vinyl alcohol copolymer, its diameter may be 0.1–0.5 mm and 0.3 mm, for example, and length may be 1–10 mm, and 5 mm, for example.

This joint member 15 is connected and fixed at its proximal end to the distal end of the wire body 10. No particular limitation is imposed on the connecting means therefor. For example, bonding with an adhesive, welding, connection by physical force or the like may be used. Of these, the bonding with an adhesive is particularly preferred. In this case, for example, a cyanoacrylate type adhesive should preferably be used.

An example of the implanted device 16 used in the present invention includes a coil piece used as a thrombus-forming member. In the present invention, for example, a double-coiled wire formed of a flexible material which is pliable should preferably be used as such a coil piece.

More specifically, a double-coiled wire which is composed of, for example, a platinum alloy, produced by winding a wire in a spiral having a diameter of 0.05 mm and has a primary coil diameter of 0.1 to 1.0 mm and a secondary coil diameter of 2 to 40 mm should preferably be used. Such an implanted device 16 may carry or hold suitable substances.

The implanted device 16 is connected to the distal end of the joint member 15. Any suitable means selected from the various means described above may be used as the connecting means between the joint member 15 and the wire body 10.

Figure 2:
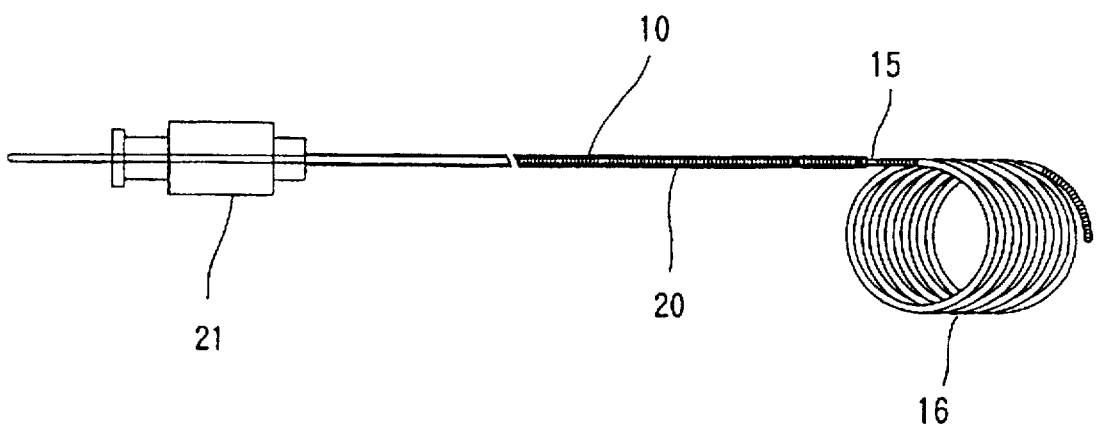
FIG. 2 illustrates an example of a specific means for implementing the medical wire of FIG. 1.
Figure 3:
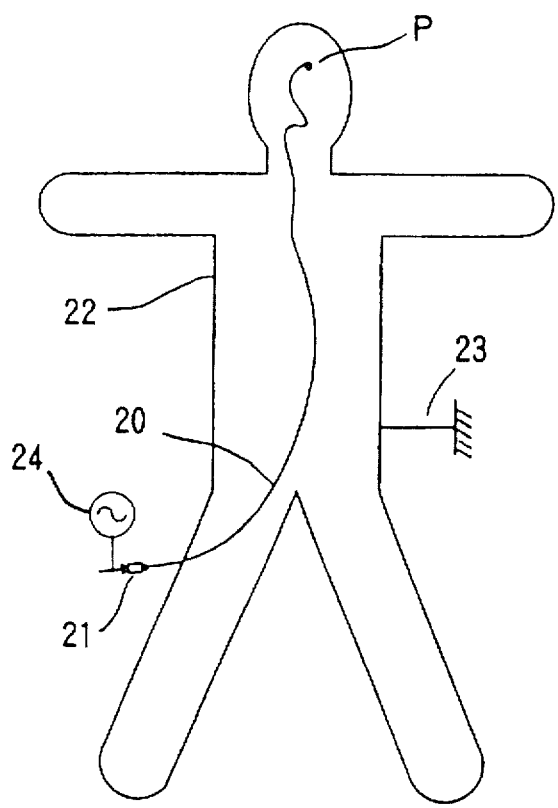
FIG. 3 schematically illustrates an instance where the medical wire according to the present invention is implemented for a cerebral aneurysm.

The medical wire of the above-described construction is inserted into a patient's body to be treated by means of a suitable catheter 20 as illustrated in FIG. 2. Specifically, the catheter 20 is inserted first in the patient's body 22 by the conventional method as illustrated in FIG. 3.

The distal end thereof is situated at the intended site at which the implanted device 16 is to be deposited, or the site P of cerebral aneurysm in this embodiment. Reference numeral 21 indicates the proximal operating part of the catheter 20. For this catheter 20, an ordinary catheter, for example, a micro catheter can be used.

In this state, the medical wire is inserted into the catheter 20 through the proximal operating part 21 with the implanted device 16 in the lead. Then, the coil piece forming the implanted device 16 moves along within the catheter 20 as a single coil with the secondary coil thereof stretched in an essentially straight line along the catheter 20.

The implanted device 16 of the medical wire is ejected out the distal opening of the catheter 20 so as to situate the joint member 15 at the distal opening. As a result, the implanted device 16 returns to its original double-coiled form by the force of its elasticity to serve as a thrombus-forming member.

As illustrated in FIG. 3, an earth electrode 23 is attached to the skin surface of the patient's body 22, and a monopolar high-frequency current is applied to the wire body 10 by a high-frequency power source 24 connected to the terminal end 18 of the wire body 10.

As a result, the distal end of the wire body 10 or the joint member 15 generates its own heat with the high-frequency current with reaching a high temperature, and as a result the joint member 15 melts and severs or is deformed. Therefore, the implanted device 16 is detached from the wire body 10, whereby a thrombus-forming member composed of the coil piece can be left at the intended site in the patient's body.

According to the above described embodiment, the high-frequency current applied to the wire body 10 by the high-frequency power source 24 does not adversely affect the patient's body as long as the frequency and electric current are about 100 to 5,000 kHz and about 0.1 to 20 W, respectively.

When a material having sufficient rigidity or mechanical strength at about 35° to 37° C., which is the ordinary temperature of the human body, and a melting point of 100° C. or lower is selected as a material for the joint member 15, the joint member 15 can be heated and severed within a short period of time by applying the high-frequency current thereto.

When the joint member 15 is composed of, for example, poly(vinyl alcohol) or a vinyl alcohol copolymer, the joint member 15 can be severed by applying a high-frequency current for an extremely short period of within 1 to 3 seconds, for example. Therefore, stress imposed not only on the surgeon, but also on the patient can be greatly lightened. In addition, the possibility of metal ions is reduced, and problems of producing of fragments from the joint member can be completely eliminated, thus, alleviating greatly them, and so a possibility that contingencies may occur in the patient's body during the operation.

Since the wire body 10 is conductive, a monopolar high-frequency current can be applied to the joint member 15 through the wire body 10 effectively using its conductivity, thereby heating the joint member 15 with certainty. Therefore, there is no need for lead wires extending to the joint member 15, so that providing high operatically, and no possibility that the lead wires could break. Accordingly, even when the implanted device 16 is pulled back for the purpose of changing or correcting the position of the implanted device, such an operation can be easily performed with certainty, securing high reliability. As described above, the medical wire with an implanted device in accordance with the present invention permits safe and certain deposit of the implanted device and moreover, allows it to be pulled back and redisposed at a preferred site even after it has been disposed once in an undesirable position.

The medical wire in accordance with the present invention permits detachment of the implanted device in an extremely short period of time, and so mental and physical stress imposed on doctors and patients can be alleviated to a great extent. Moreover, its overall construction is very simple, and there is little possibility that electrical trouble such as breaking of a lead wire would occur. As a result, high reliability can be secured.

Figure 4:
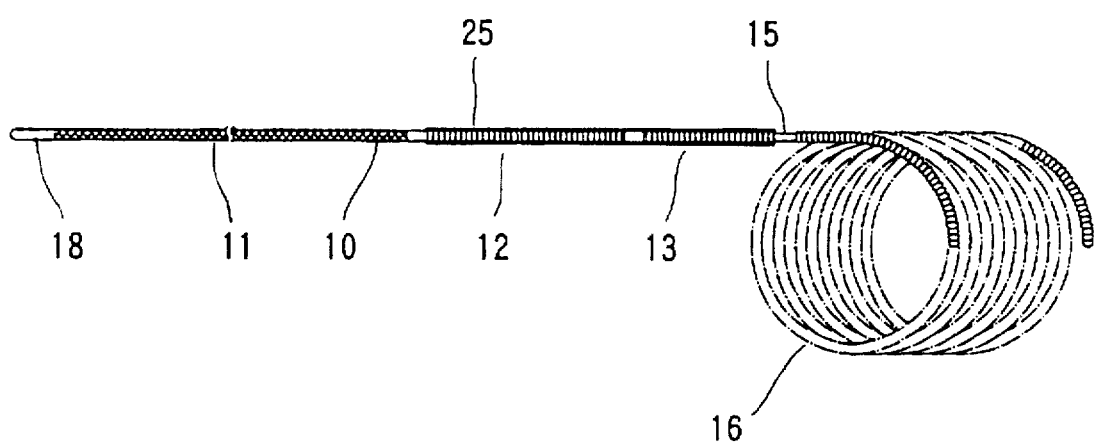
FIG. 4 illustrates the construction of a medical wire which is another embodiment of the present invention.

FIG. 4 illustrates another embodiment of the present invention. In this embodiment, an electrically insulated coating 25 is provided on the peripheral surfaces of the flexible part 12 and distal X-ray impervious part 13 in the wire body 10. This electrically insulated coating 25 can be formed by one of various polymers, for example, fluorocarbon resins, polyurethane, polyethylene, polypropylene, silicone resins and polyamide resins, such as nylon. A hydrophilic polymer may be further provided on the coating of this resin.

According to the medical wire of such a construction, the implanted device 16 can be detached and left by applying a monopolar high-frequency current through the wire body 10 like the above-described embodiment, and the vital tissue would be protected from adverse effects because almost the entire surface of the wire body 10, with which the body tissue is brought into contact, is covered with the electrically insulating coating 25.

For this reason, the medical wire may be inserted into the patient's body without using any catheter.

The present invention will hereinafter be described more specifically by the following experimental example. However, the present invention is not limited to or by this example.

Experimental Example

Following the construction of FIG. 1, a wire having a diameter of 0.08 mm was wound on part of the peripheral surface of a tapered core wire having a diameter of 0.05-0.40 mm, thereby producing a wire body 10 made of stainles steel having an overall diameter of 0.4 mm and an overall length of 1,800 mm. Bonded to the distal end of the wire body 10 with a cyanoacrylate type adhesive was the proximal end of a joint member 15 composed of a vinyl alcohol copolymer having a melting point of 80° C. in the form of a columnar rod having a diameter of 0.3 mm and a length of 10 mm. Further bonded to the distal end of the joint member 15 with a cyanoacrylate type adhesive was the end of an implanted device 16 composed of a double-coiled wire constructed of a platinum alloy wire having a diameter of 0.05 mm, and having a primary coil diameter of 0.4 mm and a secondary coil diameter of 3-12 mm, thereby producing the medical wire.

As illustrated in FIG. 5, a stainless steel container 30 equipped with an earth electrode 31 was filled with physiological saline 32, and a micro catheter 33 having an outer diameter of 1 mm and an overall length of 1,500 mm was fixed to the container 30 with the distal end of the catheter dipped into the physiological saline 32.

The medical wire was then inserted into the micro catheter 33 through the proximal operating part 34 of the micro catheter 33 outside the container 30 with the implanted device 16 in the lead and advanced until the joint member 15 reached the position of the distal opening of the micro catheter 33. As a result, the implanted device 16 completely returned to the double-coiled original form.

In this state, an output terminal of a high-frequency power source 35 was connected to a terminal end 18 situated at the proximal end of the wire body 10 in order to apply a high-frequency current of a frequency of 300 kHz and electric power of 5.5 W. As a result, the joint member 15 was instantaneously melted and severed to detach the implanted device 16 from the wire body 10.

Although the embodiments of the present invention have been described above, numerous modifications and variations may be made to the present invention. For example, the wire body 10 may be composed of a single wire or a bundle of wires, or may be a wire composed of multiple wire segments of suitable lengths connected in series.

In the present invention, various kinds of implanted device may be employed. Specifically, thrombus-forming devices in the form of a coil piece or forms other than the coil piece, such as capsules containing a drug therein, which are left in the patient's body to gradually release the drug, embolizing devices for occluding tubular organs, such as balloons, as well as suitable devices which perform a medical function or medically auxiliary function while implanted.

What is claimed is:

1. A medical wire for depositing an implanted device, comprising:

a conductive wire body; and a joint member for connecting the implanted device to a distal end of the conductive wire body;

wherein the joint member comprises a material which may be heated by a monopolar high-frequency current applied through the conductive wire body so that the implanted device becomes detached from the conductive wire body.

2. The medical wire according to claim 1, wherein the joint member comprises one of polyvinyl alcohol and a vinyl alcohol copolymer, and wherein the joint member is severed upon being heated.

3. The medical wire according to claim 1, wherein the conductive wire body comprises a wire wound to form a coil on a peripheral surface of a core wire.

4. The medical wire according to claim 1, wherein a surface of the conductive wire body is covered with an electrically insulated coating.

5. The medical wire according to claim 1, wherein the implanted device comprises a coil piece formed of a flexible material which is pliable.

6. The medical wire according to claim 2, wherein the conductive body wire comprises a wire wound to form a coil on a peripheral surface of a core wire.

7. The medical wire according to claim 2, wherein a surface of the conductive wire body is covered with an electrically insulated coating.

8. The medical wire according to claim 3, wherein a surface of the conductive wire body is covered with an electrically insulated coating.

9. The medical wire according to claim 6, wherein a surface of the conductive wire body is covered with an electrically insulated coating.

10. The medical wire according to claim 2, wherein the implanted device comprises a coil piece formed of a flexible material which is pliable.

11. The medical wire according to claim 3, wherein the implanted device comprises a coil piece formed of a flexible material which is pliable.

12. The medical wire according to claim 6, wherein the implanted device comprises a coil piece formed of a flexible material which is pliable.

13. The medical wire according to claim 4, wherein the implanted device comprises a coil piece formed of a flexible material which is pliable.

14. The medical wire according to claim 7, wherein the implanted device comprises a coil piece formed of a flexible material which is pliable.

15. The medical wire according to claim 8, wherein the implanted device comprises a coil piece formed of a flexible material which is pliable.

16. The medical wire according to claim 9, wherein the implanted device comprises a coil formed of a flexible material which is pliable.

17. A method for depositing an implanted device in a patient's body, comprising the following steps:

inserting a medical wire through a vital tubular organ to thereby guide the implanted device to an intended site in the patient's body, said medical wire comprising a conductive wire body and a joint member for connecting the implanted device to a distal end of the conductive wire body; and applying a monopolar high-frequency current to the joint member through the conductive wire body, thereby heating the joint member so as to cause the joint member to melt and sever, whereby the implanted device is detached from the conductive wire body.

18. The method according to claim 17, wherein the frequency and electrical current of the monopolar high-frequency current are 100 to 5,000 kHz and 0.1 to 20 W, respectively.

* * * * *